(12) United States Patent
Kim

(10) Patent No.: US 11,648,413 B2
(45) Date of Patent: May 16, 2023

(54) METHOD AND APPARATUS FOR STIMULATING VAGUS NERVE USING PULSED ELECTROMAGNETIC FIELD

(71) Applicant: Amo Lab Co., Ltd., Seongnam (KR)

(72) Inventor: Min Kyu Kim, Anyang (KR)

(73) Assignee: Amo Lab Co., Ltd., Seongnam (KR)

(*) Notice: Subject to any disclaimer, the term of this patent is extended or adjusted under 35 U.S.C. 154(b) by 453 days.

(21) Appl. No.: 16/310,799

(22) PCT Filed: Sep. 4, 2018

(86) PCT No.: PCT/KR2018/010249
§ 371 (c)(1),
(2) Date: Dec. 17, 2018

(87) PCT Pub. No.: WO2019/164076
PCT Pub. Date: Aug. 29, 2019

(65) Prior Publication Data
US 2021/0220663 A1    Jul. 22, 2021

(30) Foreign Application Priority Data
Feb. 23, 2018 (KR) .......... 10-2018-0021853

(51) Int. Cl.
*A61N 2/02* (2006.01)
*A61N 2/00* (2006.01)
(52) U.S. Cl.
CPC ............. *A61N 2/02* (2013.01); *A61N 2/006* (2013.01)

(58) Field of Classification Search
CPC ................................. A61N 2/00–12
See application file for complete search history.

(56) References Cited

U.S. PATENT DOCUMENTS

| 7,175,587 | B2 | 2/2007 | Gordon et al. | |
| 2005/0182287 | A1* | 8/2005 | Becker | A61N 2/02 336/122 |
| 2008/0125618 | A1* | 5/2008 | Anderson | A61N 2/02 607/51 |
| 2010/0130945 | A1* | 5/2010 | Laniado | A61N 2/02 604/290 |
| 2011/0125203 | A1* | 5/2011 | Simon | A61N 1/40 607/2 |
| 2013/0261374 | A1 | 10/2013 | Elder | |
| 2016/0220838 | A1* | 8/2016 | Scheinowitz | A61N 2/02 |
| 2016/0271394 | A1* | 9/2016 | Sunagawa | A61N 1/36053 |
| 2020/0046968 | A1* | 2/2020 | Herr | C12N 15/86 |

* cited by examiner

*Primary Examiner* — Thaddeus B Cox

(57) ABSTRACT

The present invention relates to a method and apparatus for simulating the vagus nerve. The apparatus for stimulating the vagus nerve includes: a magnetic field generation unit generating a magnetic field in a form of pulse, which stimulates a preset area including the vagus nerve of a user by an electric current applied to a coil; a power supply unit applying the electric current to the coil; and a control unit controlling an intensity of the electric current applied to the coil, and a pulse width and a peak interval of the magnetic field, wherein the magnetic field has a peak intensity that is set using a biomagnetic signal of the use. According to the present invention, the body function may be improved using the pulsed magnetic field with the intensity close to the biomagnetic signals.

11 Claims, 5 Drawing Sheets

METHOD AND APPARATUS FOR STIMULATING VAGUS NERVE USING PULSED ELECTROMAGNETIC FIELD

CROSS-REFERENCE TO RELATED APPLICATIONS

This application is a U.S. National Phase of International Application No. PCT/KR2018/010249, filed Sep. 4, 2018, which claims priority to Korean Patent Application No. 10-2018-0021853, filed Feb. 23, 2018, the entire contents of which are hereby incorporated by reference.

TECHNICAL FIELD

The present invention relates generally to a method and apparatus for stimulating the vagus nerve. More particularly, the present invention relates to a method and apparatus for stimulating the vagus nerve using a pulsed magnetic field.

BACKGROUND ART

Generally, a magnetic field causes the magnetic flux to permeate from the epidermis to deep tissues (blood vessels, bone joints, and the like) irrespective of the characteristics of the medium so as to increase vigor of the blood flow. Also, it is known that oxygen and nutrients in the blood are binded and transported to each cellular tissue and organ for taking charge of metabolism and blood circulation is promoted to quickly remove waste products in the body such that diseases are prevented.

For this reason, various therapy devices have been developed to stimulate human body tissues using a magnetic field so as to treat pain, diseases, and the like. A method of treating soft tissue trauma as disclosed in U.S. Pat. No. 7,175,587 (title: Method and apparatus for pulsed electromagnetic therapy, publication date: Feb. 13, 2007) and devices that are useful for osteoporosis therapy, arthritis, rheumatism, vasodilation, and the like as disclosed in United States Patent Application No. 20130261374 (title: Device and method for generating magnetic fields, publication date: Jun. 7, 2012) have been developed.

However, these conventional electromagnetic therapy devices use magnetic fields with the intensity in Gaussian units. Therefore, when an error occurs in the amplitude of the pulse or operation time, it may have harmful effects on the human body. Thus, it is necessary to precisely control the duration time. Further, most electromagnetic therapy devices tend to be limited to the treatment of bone or soft tissue, so that the utilization is limited.

DISCLOSURE

Technical Problem

Accordingly, the present invention has been made keeping in mind the above problems, and the present invention is intended to propose a method and apparatus for improving body function by using a pulsed magnetic field with the intensity close to biomagnetic signals.

Also, the present invention is intended to enhance sleep quality, relieve stress, stabilize the heart rate and respiration, and so on using the pulsed magnetic field so as to prevent and treat diseases related to the vagus nerve.

Technical Solution

In order to achieve the above object, the present invention provides an apparatus for stimulating the vagus nerve, the apparatus including: a magnetic field generation unit generating a magnetic field in a form of pulse, which stimulates a preset area including the vagus nerve of a user by an electric current applied to a coil; a power supply unit applying the electric current to the coil; and a control unit controlling an intensity of the electric current applied to the coil, and a pulse width and a peak interval of the magnetic field, wherein the magnetic field has a peak intensity that is set using a biomagnetic signal of the user.

Also, there is provided a method of stimulating vagus nerve, the method including: positioning a coil within a preset area including the vagus nerve of a user; and generating a magnetic field in a form of pulse, which stimulates the area by applying an electric current to a coil, wherein the magnetic field has a peak intensity that is set using a biomagnetic signal of the user.

Advantageous Effects

According to the present invention as described above, the body function may be improved using the pulsed magnetic field with the intensity close to the biomagnetic signals.

According to the present invention, by using the pulsed magnetic field, sleep quality is enhanced, stress is relieved, the heart rate and respiration are stabilized, and so on, whereby the diseases related to the vagus nerve are prevented and treated.

MODE FOR INVENTION

Figure 1:
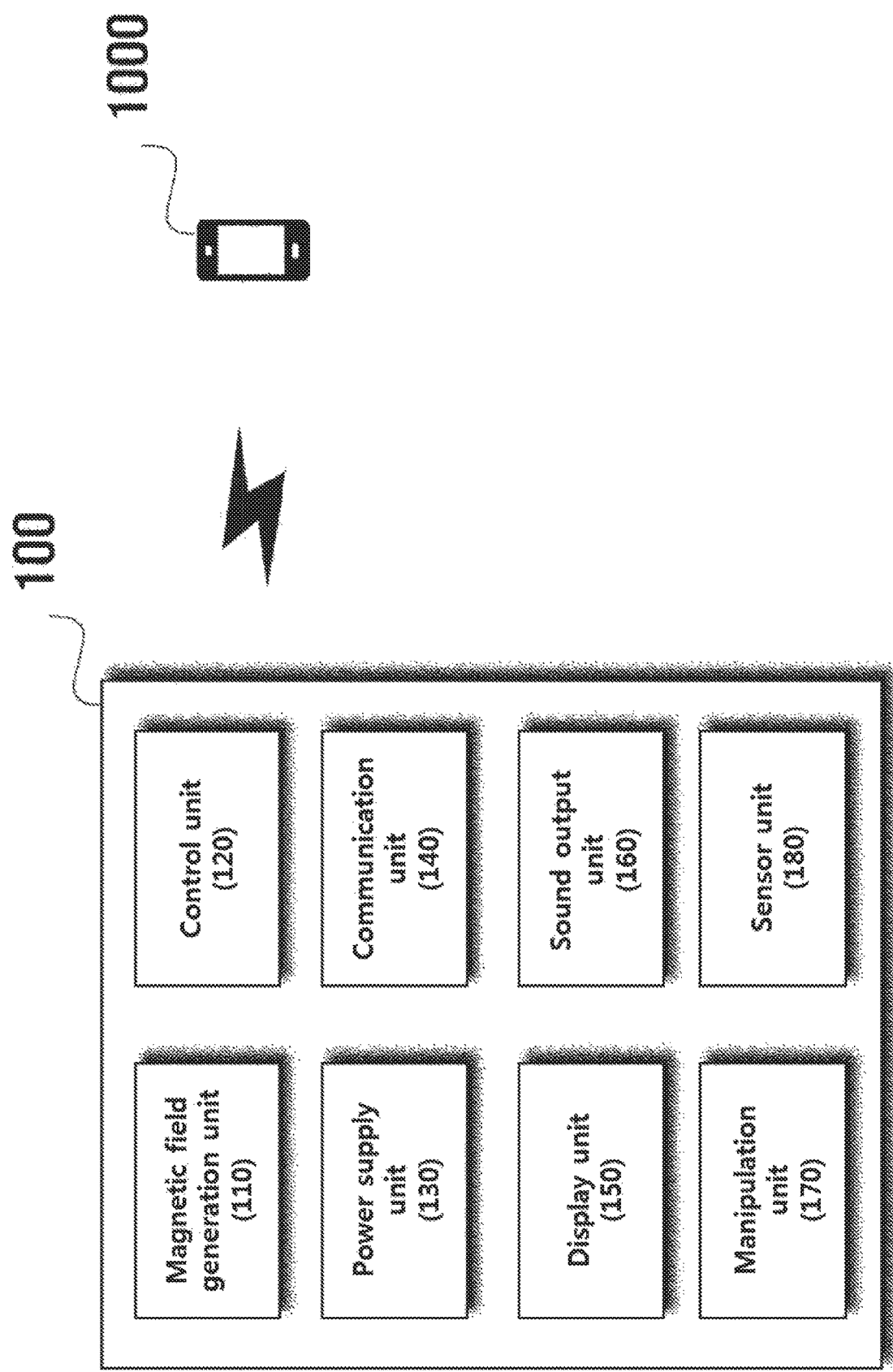
FIG. 1 is a block diagram illustrating a configuration of an apparatus for stimulating the vagus nerve according to an embodiment of the present invention.

The above-described objects, features, and advantages will be described in detail with reference to the accompanying drawings. Accordingly, the technical scope of the present invention can be easily embodied by those skilled in the art to which the present invention belongs. In describing the present invention, it is decided that if detailed description of the known art related to the present invention makes the subject matter of the present invention unclear, the detailed description will be omitted. Hereinafter, preferred embodiments of the present invention will be described with reference to the accompanying drawings. The same reference numerals are used throughout the drawings to refer to the same or like elements. All combinations described in the specification and the appended claims can be combined in arbitrary manner. Further, it is understood that unless specifically stated otherwise, references to "a", "an", and/or "the" may include one or more than one, and that reference to an item in the singular may also include the item in the plural.

FIG. 1 is a block diagram illustrating a configuration of an apparatus for stimulating the vagus nerve according to an embodiment of the present invention. Referring to FIG. 1, according to the embodiment of the present invention, the apparatus for stimulating the vagus nerve includes a magnetic field generation unit 110, a control unit 120, and a power supply unit 130, and further includes a communication unit 140, display unit 150, a sound output unit 160, a manipulation unit 170, and a sensor unit 180.

Figure 2:
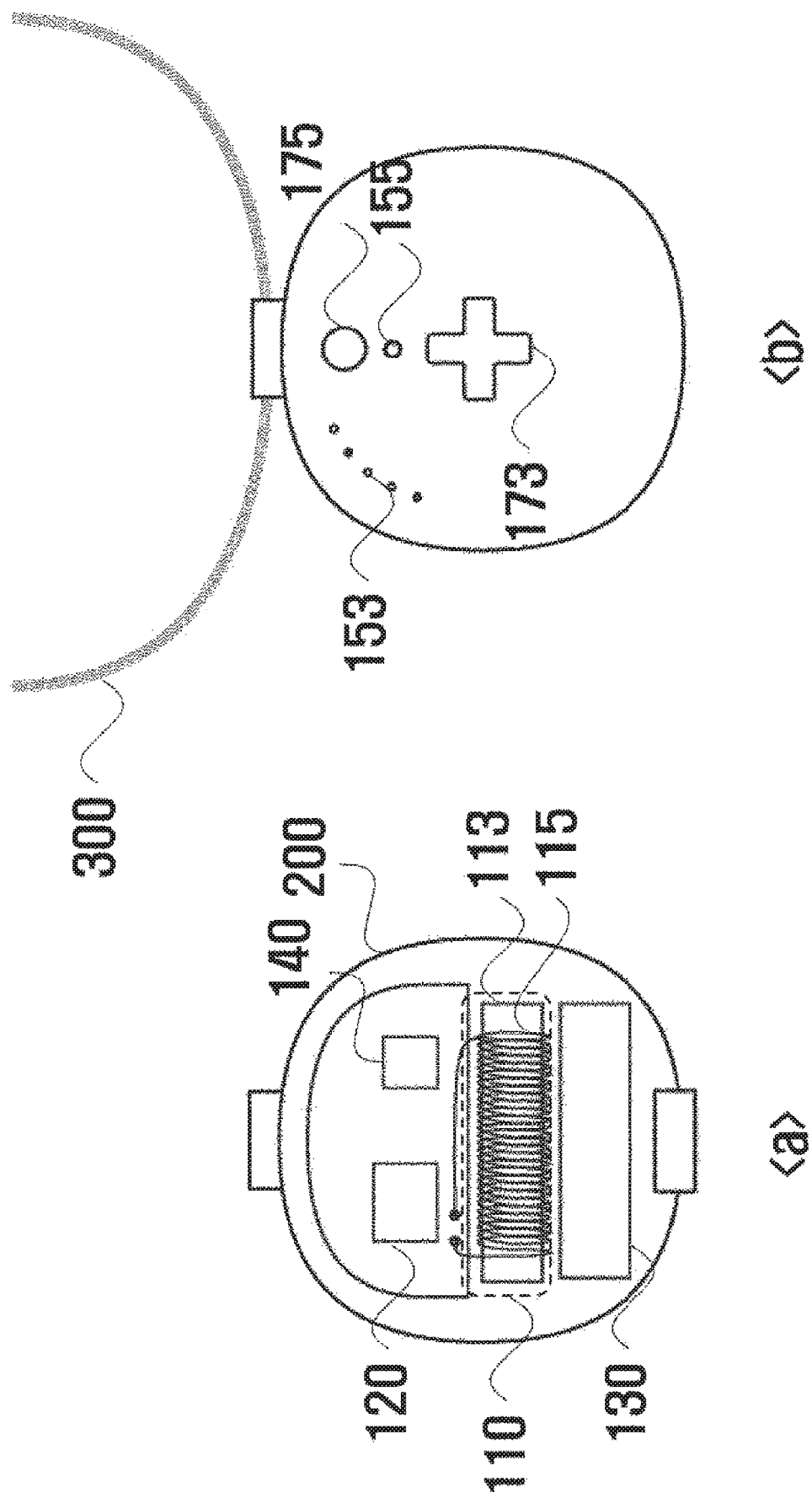
FIG. 2 is a diagram illustrating operation of an apparatus for stimulating the vagus nerve according to an embodiment of the present invention.

The magnetic field generation unit 110 may be an inductor, which generates a pulsed magnetic field that stimulates a preset area including the user's vagus nerve by an electric current applied to a coil. More specifically, the magnetic field generation unit 110 may include a coil 115 and a silicon steel plate 113 around which the coil is wound as shown in FIG. 2. The silicon steel plate may be replaced by a non-conductive or conductive material, and in the embodiment of the present invention, the length may be 10 to 60 mm, the width may be 10 to 60 mm, and the thickness may be 0.1 to 5 mm. A wire that is used as the coil 115 wound around the silicon steel plate 113 may be 0.1 to 0.8 mm in diameter, and preferably is 0.2 to 0.4 mm in diameter. The coil is wound around the silicon steel plate 113 100 to 600 times and generates the magnetic field with the electric field intensity (the peak intensity equal to or less than 100 microtesla) according to the embodiment of the present invention.

The magnetic field generation unit 110 is required to be positioned within the preset area including the vagus nerve such that the magnetic field generated by the magnetic field generation unit 110 reaches the user's vagus nerve. That is, it is desirable that the magnetic field generation unit 110 is positioned in such a manner as to include the user's vagus nerve within an effective radius of the magnetic field, and the effective radius may be about 30 cm.

Further, the intensity of the magnetic field may be set according to the position of the magnetic field generation unit 110 in such a manner that the magnetic field of a particular intensity stimulates the vagus nerve using the intensity of the magnetic field generated by the magnetic field generation unit 110 and the distance to the vagus nerve. This is because the intensity of the magnetic field decreases in inverse proportion to the square of the distance to the target to be stimulated.

That is, the peak intensity of the magnetic field, which is generated by the apparatus for stimulating the vagus nerve according to the embodiment of the present invention, may be set using the distance between the magnetic field generation unit and the user's vagus nerve and the intensity corresponding to the magnetic signal of the vagus nerve, and may be set in such a manner that the intensity of the magnetic field which reaches the vagus nerve corresponds to the intensity of the magnetic field which is generated in the vagus nerve.

As another embodiment, the peak intensity may be set using the distance between the magnetic field generation unit and the user heart and the intensity corresponding to the magnetic signal of the heart, and may be set in such a manner that the intensity of the magnetic field which reaches the heart corresponds to the intensity of the magnetic field which is generated in the heart. Since the heart and the vagus nerve are connected to each other, the apparatus for stimulating the vagus nerve of the present invention enables the pulsed magnetic field to reach the vagus nerve branch connected to the heart.

For example, it is known that the magnetic signal of the heart and/or the vagus nerve connected to heart which is measured by a SQUID (superconducting quantum interference device) has the intensity of 10 pT to 0.01 µT. The apparatus for stimulating the vagus nerve according to the embodiment of the present invention may be set the peak intensity of the magnetic field generated by the magnetic field generation unit 110 in such a manner that when the magnetic field generated by the magnetic field generation unit 110 reaches the heart or the vagus nerve connected to the heart, the intensity corresponding to the biomagnetic signals is able to stimulate the heart and/or the vagus nerve. The magnetic field generation unit 110 may be positioned near the user's chest in the form of a necklace or a clip. Thus, in this example, the peak intensity of the magnetic field generated by the magnetic field generation unit 110 may be in a range of 0.01 µT to 100 µT. Here, the peak intensity of the magnetic field may be set on the basis of the intensity measured at the end of the coil.

This is to induce magnetic field synchronization by causing the magnetic field that reaches the heart or the vagus nerve to have the similar or equal magnetic field intensity and/or frequency to the biomagnetic signal (magnetic field) generated in the heart or the biomagnetic signal (magnetic field) generated in the vagus nerve. When the magnetic field synchronization occurs, there are effects of improving and/or restoring the balance of the autonomic nervous system, such as enhancing sleep quality, reducing stress, stabilizing the heart rate and respiration, and the like. These effects have been demonstrated in clinical experiments, and the results of the experiments will be described later.

The control unit 120 may control the intensity of the electric current applied to the coil 115, and the pulse width and the peak interval of the magnetic field. The intensity of the electric current may be determined according to the electric field intensity of the set magnetic field, and the pulse width of the magnetic field may be determined within a range of 10 to 200 µs as shown in FIG. 4.

Figure 4:
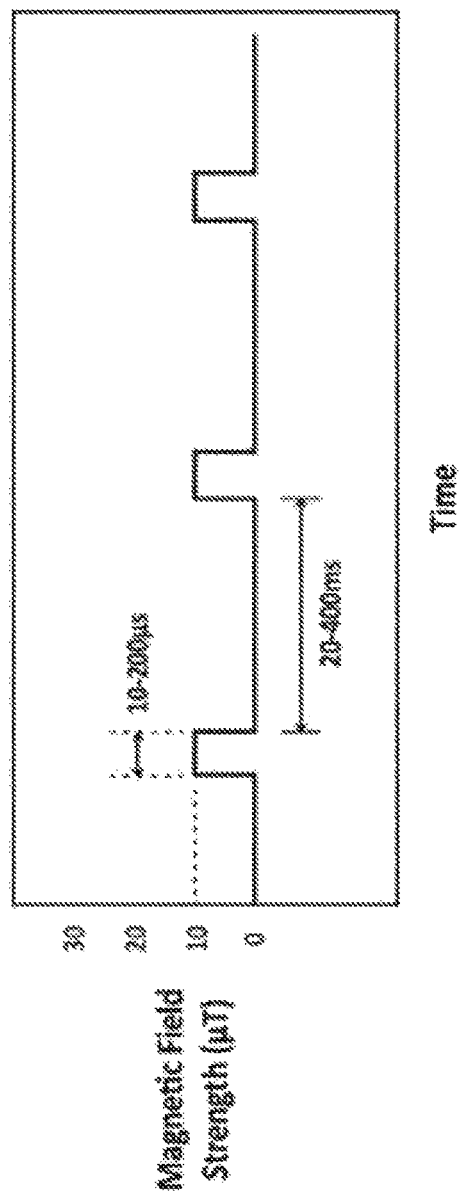
FIG. 4 is a diagram illustrating a characteristic of a magnetic field that occurs in an apparatus for stimulating the vagus nerve according to an embodiment of the present invention.

In order to derive the autonomic nervous system stabilization effect according to the embodiment of the present invention, the control unit 120 may set the period of the pulsed magnetic field in such a manner that the peak interval is in a rage of 20 to 400 ms as shown in FIG. 4. Further, as described above, the control unit 120 may set the peak intensity of the pulsed magnetic field within a range of 0.01 to 100 µT. Furthermore, the control unit 120 may set the magnetic field in such a manner as to be repeated with a frequency of 1 to 8 Hz, particularly to have the frequency corresponding to the heart and/or the vagus nerve connected to the heart.

In the present invention, the apparatus 100 for stimulating the vagus nerve stimulates the heart and/or the vagus nerve branch connected to the heart and synchronizes the magnetic field generated in the apparatus 100 for stimulation with the biomagnetic signal generated in the user as described above. Therefore, the control unit 120 is required to set the frequency in such a manner that the pulsed magnetic field generated by the magnetic field generation unit 110 is synchronized with the biomagnetic signal of the user.

The normal heat beat frequency of a human is known as 7 to 8 Hz. When an imbalance of the human body function occurs, the natural frequency of the human body is disturbed and lowered to 7 Hz or less. According to the embodiment of the present invention, the apparatus 100 for stimulating the vagus nerve subjects the distorted frequency of the human body, which is caused by the function imbalance as described above, to a phenomenon of synchronization in such a manner that the distorted frequency is restored into the original natural frequency. Accordingly, the control unit 120 may set the frequency of the pulsed magnetic field in such a manner as to have the frequency corresponding to the distorted frequency, and the set frequency is in a range of 1 to 8 Hz.

The control unit 120 may output the pulsed magnetic field having the intensity, the pulse width, and the frequency in a single or multiple manners, and may output two or more multi-frequencies in order. The control unit 120 may receive setting information from the manipulation unit 170 or communication unit 140 and may control the intensity of the electric current applied to the coil in such a manner as to generate the magnetic field corresponding to the received setting information.

Figure 5:
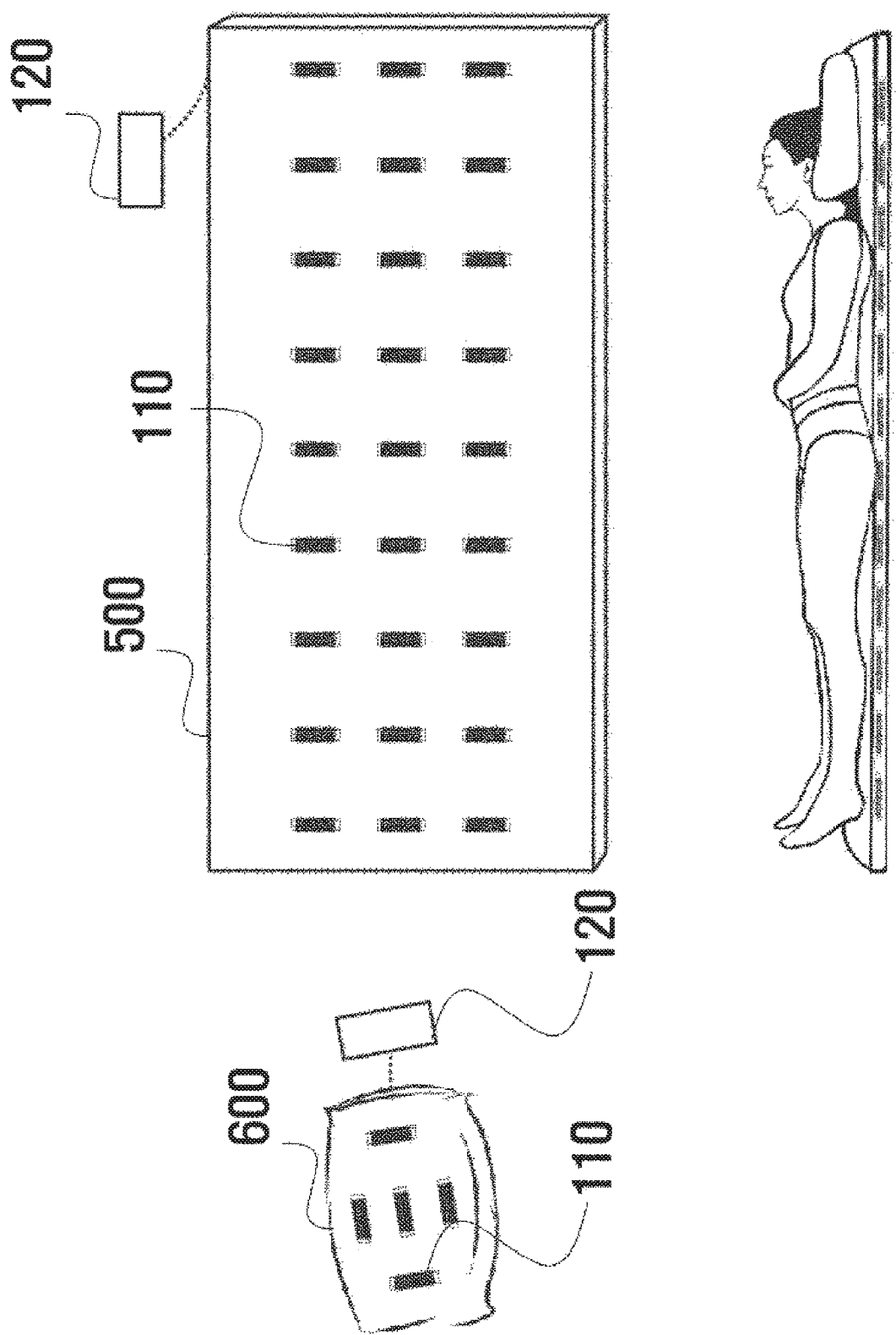
FIG. 5 is a diagram illustrating an example of utilization of an apparatus for stimulating the vagus nerve according to an embodiment of the present invention.

The power supply unit 130 applies the electric current to the coil 115. The power supply unit 130 may be a rechargeable battery that receives power from an external power source for storage and supplies the electric current to the coil 115 when the apparatus 100 for stimulating the vagus nerve operates. According to the embodiment of the present invention, the apparatus for stimulating the vagus nerve may be realized in the form of the necklace, the clip, or the patch, and in this case, the power supply unit 130 may be embedded within the apparatus 100 in the form of a rechargeable battery. The power supply unit 130 may be realized in the form of an adaptor that receives power from the external power source and applies the electric current to the coil 115 when the apparatus 100 for stimulating the vagus nerve is embedded in a pillow or a blanket as shown in FIG. 5.

The communication unit 140 may receive, from a terminal 1000, setting information including the peak intensity, the pulse width, and the frequency of the magnetic field, and the operation of the apparatus for transmission to the control unit 120. The communication unit 140 may transmit, to the terminal 1000, apparatus information including the use time, the use pattern of the apparatus 100 for stimulating the vagus nerve, the intensity, the pulse width, the frequency of the generated magnetic field, the remaining battery life, the type (single/multiple) of pulse sequence, occurrence of error, and the like.

The communication unit 140 may include: a mobile communication module supporting data transmission and reception according to a technical standard or communication methods for mobile communication (for example, GSM, CDMA, WCDMA, LTE, and the like); a wireless Internet module supporting communication methods, such as WLAN, WiFi, DLNA, Wimax, HSDPA, and the like; a short-range communication module supporting short-range communication, such as Bluetooth, RFID, IrDA, ZigBee, NFC, Wi-Fi Direct, and the like; and/or a location information module such as the GPS.

The display unit 150 may be an LED or display module that displays the set information. For example, as shown in FIG. 2, according to the embodiment of the present invention, the remaining operation time of the apparatus 100 may be expressed as the number of LED lamps 153, and whether the apparatus operates or not may be expressed as the color of an LED lamp 155. As another embodiment, although not shown in the drawings, when the display module is used, information such as the intensity of the magnetic field, the pulse width, the frequency, the operation time, the remaining battery life, and the like is displayed on the display module as text or an image.

The sound output unit 160 may output audio data that is received from the communication unit 140 or is stored in a storage unit (not shown). The sound output unit 160 may output sound for informing about the state of the apparatus 100, such as operation of the apparatus 100, lack of remaining battery life, and malfunction.

The manipulation unit 170 is the user interface for manipulating setting of the control unit 120, on/off of the apparatus for stimulating the vagus nerve, and the like, and may be realized in the form of a manipulation button or touch screen that is formed on a housing 200.

The sensor unit 180 may include at least one sensor that senses all bio signals that include body function states, such as the moving distance of the user who uses the apparatus for stimulating the vagus nerve, the number of steps, the body temperature, blood sugar, heart rate, calorie consumption, sleep, stress, skeletal muscle mass, skin temperature, blood flow, pulse, and the like. The sensing information obtained by the sensor may be transmitted to the terminal via the communication unit 140).

As another embodiment, the sensing information obtained by the sensor unit 180 may be transmitted to the control unit 120 to be used for apparatus control by the control unit 120. For example, when obtaining the sensing information indicating that the sympathetic nerve is activated such as increase in body temperature or blood sugar, and the like, due to the user's activity, the control unit 120 that received the sensor information automatically activates the magnetic field generation unit 110 in a stationary state, whereby the vagus nerve is stimulated.

According to the embodiment of the present invention, since the apparatus 100 for stimulating the vagus nerve stimulates the human body using the magnetic field with the intensity similar to the biomagnetic signal, there is no restriction of the use time and the user may operate the apparatus at any time desired.

FIG. 2 is a diagram illustrating operation of an apparatus for stimulating the vagus nerve according to an embodiment of the present invention. FIG. 2 illustrates an example of the apparatus for stimulating the vagus nerve, and its configuration and arrangement may be changed without limitation. FIG. 2<*a*> is a diagram illustrating the inside of the apparatus for stimulating the vagus nerve, and FIG. 2<*b*> is a diagram illustrating the outside.

According to the embodiment of the present invention, the apparatus for stimulating the vagus nerve may be realized in the form that the magnetic field generation unit 110, a power supply unit 130, and the control unit 120 are provided within the housing 200 as shown in FIG. 2. Further, included is a string member 300 that is connected to the housing 200 in such a manner as to hang the housing 200 on the user's neck and is intended to adjust the length in such a manner that the magnetic field generation unit is positioned within a preset distance from the user's vagus nerve.

Figure 3:
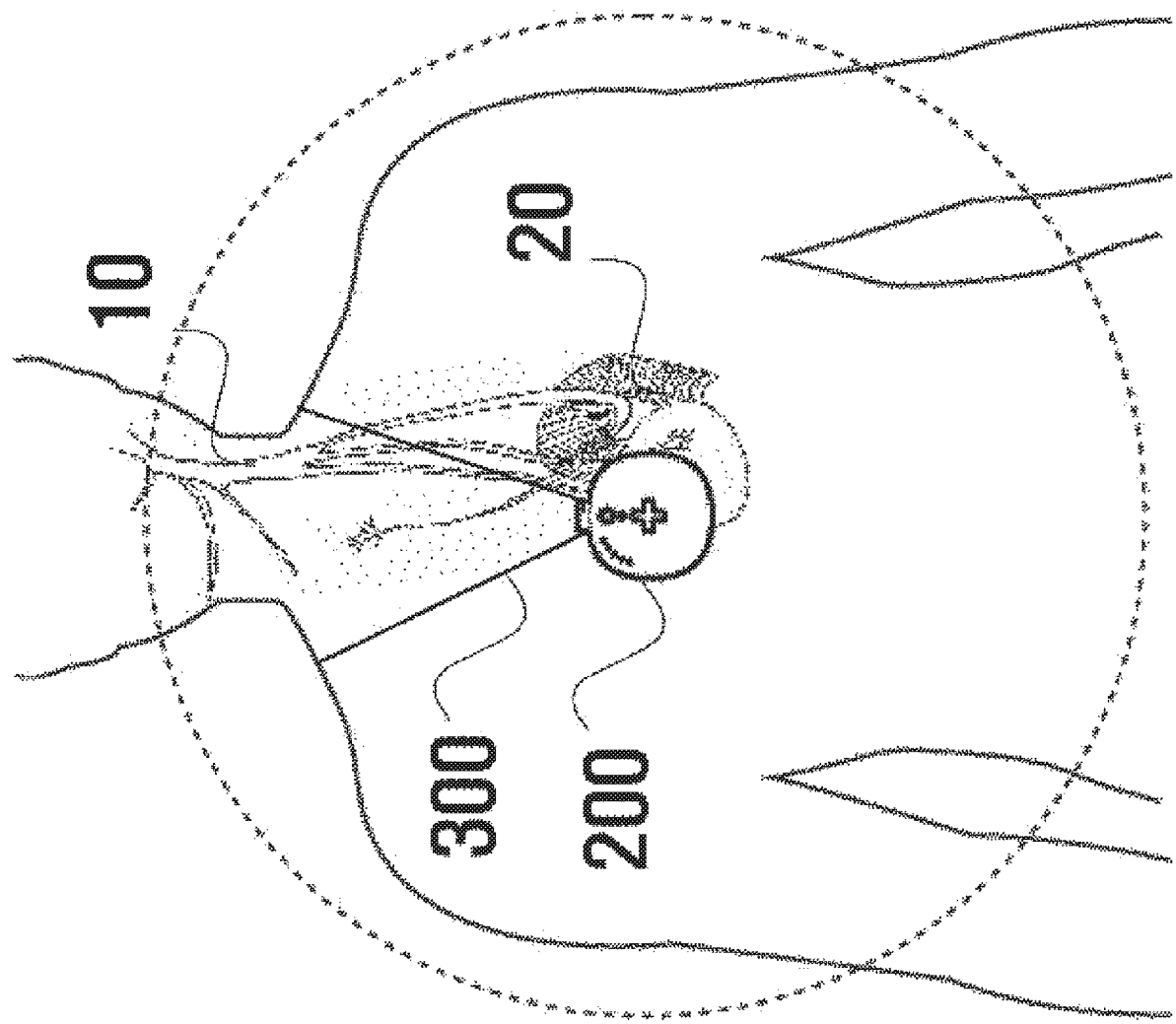
FIG. 3 is a diagram illustrating an apparatus for stimulating the vagus nerve according to an embodiment of the present invention.

FIG. 3 shows an example of the case in which the user wears the apparatus for stimulating the vagus nerve according to the embodiment of the present invention. The user may wear the apparatus 100 for stimulating the vagus nerve around the neck using the string member 300 in such a manner as to position the housing 200, namely, the magnetic field generation unit 110 near the heart. The magnetic field effective radius of the magnetic field generation unit 110 is about 30 cm, so that the vagus nerve 10 and the heart 20 may be influenced by the magnetic field generated by the magnetic field generation unit 110.

As another embodiment, the apparatus 100 for stimulating the vagus nerve may be attached on the chest in the form of a patch or may be attached to the clothing or the like in the form of a clip to be positioned near the chest.

That is, according to the embodiment of the present invention, in the method of stimulating the vagus nerve, the coil is positioned within the preset area including the user's vagus nerve, and the electric current is applied to the coil, there by generating the magnetic field in the form of a pulse, which stimulates the area. Here, the generated pulsed magnetic field may have the peak intensity that is set using the biomagnetic signal of the user.

As shown in FIG. 5, the apparatus 100 for stimulating the vagus nerve may be realized in a manner that magnetic field generation units 110 are arranged at preset intervals in a blanket or pillow. In this case, the control unit 120 and the power supply unit 130 may be provided within a separate housing.

According to the embodiment of the present invention, the apparatus 100 for stimulating the vagus nerve has demonstrated the immediate effect by measuring heart rate variability (HRV) before wearing the apparatus 100 and after 30 minutes of the wearing in a clinical study of 48 subjects ranging in age from twenty to sixty. Hereinafter, with reference to Tables 1 to 6, the effects of the apparatus 100 for stimulating the vagus nerve according to the embodiment of the present invention will be described.

Table 1 shows the changes in RMSSD before and after using the apparatus 100 for stimulating the vagus nerve. The RMSSD (root mean square of the successive differences) is a numerical value indicating short-term variation of the heart rate and is a primary time series measurement value used to predict the variation between heartbeats with the high frequency band in heart rate variability. The RMSSD indicates whether the parasympathetic nerve system for the heart is well controlled, and when the value is large, it is interpreted as the healthy state. Referring to Table 1 below, when using the apparatus 100 for stimulating the vagus nerve of the present invention, it was found that for all ages, the RMSSD increased at the rate of change which exceeding 74% on average. The degree of change was greater in the older age group.

TABLE 1

| | | Mean RMSSD (ms) | | |
| --- | --- | --- | --- | --- |
| Age | Gender | Before use | After use | Rate of change (%) |
| Twenties | Male (n = 5) | 40.3 | 58.2 | 44.42% |
| | Female (n = 5) | 42.8 | 61.1 | 42.76% |
| Thirties | Male (n = 7) | 31.6 | 53.0 | 67.72% |
| | Female (n = 3) | 34.3 | 59.5 | 73.47% |
| Forties | Male (n = 4) | 26.7 | 47.9 | 79.40% |
| | Female (n = 3) | 29.4 | 54.4 | 85.03% |
| Fifties | Male (n = 8) | 19.8 | 35.4 | 78.79% |
| | Female (n = 5) | 22.0 | 42.1 | 91.36% |
| Sixties | Male (n = 4) | 17.7 | 32.8 | 85.31% |
| | Female (n = 4) | 18.1 | 35.5 | 96.13% |

Table 2 shows the high frequency band (HF). The high frequency band is a frequency domain between 0.15 to 0.4 Hz, which is related to heart rate variability associated with a respiratory cycle, and this frequency band shows the activity of the parasympathetic nerve or vagus nerve.

Referring to Table 2, it was found that for all ages, the HF was also increased by 40% or more on average and relatively large changes took place in older age groups. That is, according to the apparatus 100 for stimulating the vagus nerve of the present invention, it is understood that the parasympathetic nerve is activated.

TABLE 2

| | | Mean HF (ms^2) | | | | |
| --- | --- | --- | --- | --- | --- | --- |
| Age | Gender | Before use | Before use (Ln) | After use | After use (Ln) | Rate of change (%) |
| Twenties | Male (n = 5) | 141 | 4.95 | 415 | 6.03 | 21.81% |
| | Female (n = 5) | 177 | 5.18 | 491 | 6.20 | 19.71% |
| Thirties | Male (n = 7) | 93 | 4.53 | 344 | 5.84 | 28.86% |
| | Female (n = 3) | 120 | 4.79 | 381 | 5.94 | 24.13% |
| Forties | Male (n = 4) | 42 | 3.74 | 212 | 5.36 | 43.31% |
| | Female (n = 3) | 58 | 4.06 | 297 | 5.69 | 40.22% |
| Fifties | Male (n = 8) | 29 | 3.37 | 178 | 5.18 | 53.89% |
| | Female (n = 5) | 33 | 3.50 | 225 | 5.42 | 54.90% |
| Sixties | Male (n = 4) | 23 | 3.14 | 170 | 5.14 | 63.80% |
| | Female (n = 4) | 29 | 3.37 | 206 | 5.33 | 58.22% |

Table 3 shows the LF/HF ratio before and after using the apparatus 100 for stimulating the vagus nerve of the present invention. The LF/HF ratio is the ratio of low frequency band to high frequency band in power. When the value is low, it means that the parasympathetic nerve is activated or the activity of the sympathetic nerve is inhibited. The LF/HF Ratio is an index quantifying the overall balance between the sympathetic nerve system and the parasympathetic nerve system.

Referring to Table 3, when using the apparatus 100 for stimulating the vagus nerve of the present invention, it was found that the value of the LF/HF ratio is decreased by 36% on average. That is, this indicates that the parasympathetic nerve is relatively more activated. When the parasympathetic nerve is activated, cardiac output and peripheral blood vessel resistance are reduced so that the blood pressure is reduced, which helps reliving stress and enhancing sleep quality.

TABLE 3

| | | Mean LF/HF Ratio (%) | | | | |
| --- | --- | --- | --- | --- | --- | --- |
| Age | Gender | Before use | Before use (Ln) | After use | After use (Ln) | Rate of change (%) |
| Twenties | Male (n = 5) | 2.81 | 1.03 | 1.75 | 0.56 | −45.84% |
| | Female (n = 5) | 1.67 | 0.51 | 1.32 | 0.28 | −45.86% |
| Thirties | Male (n = 7) | 3.88 | 1.36 | 2.27 | 0.82 | −39.54% |
| | Female (n = 3) | 2.26 | 0.82 | 1.71 | 0.54 | 34.20% |
| Forties | Male (n = 4) | 4.20 | 1.44 | 2.56 | 0.94 | −34.50% |
| | Female (n = 3) | 2.41 | 0.88 | 1.88 | 0.63 | −28.23% |
| Fifties | Male (n = 8) | 4.47 | 1.50 | 2.73 | 1.00 | −32.93% |
| | Female | 2.76 | 1.02 | 1.97 | 0.68 | −33.21% |

TABLE 3-continued

Mean LF/HF Ratio (%)

| Age | Gender | Before use | Before use (Ln) | After use | After use (Ln) | Rate of change (%) |
|---|---|---|---|---|---|---|
| Sixties | Male (n = 5) | 4.81 | 1.57 | 2.76 | 1.02 | −35.36% |
| | Female (n = 4) | 3.01 | 1.10 | 2.14 | 0.76 | −30.96% |
| | (n = 4) | | | | | |

Table 4 shows the mean heart rate (beats/min) before and after using the apparatus 100 for stimulating the vagus nerve of the present invention. When the mean heart rate is lowered, it means that the parasympathetic nerve system is activated. As the result of the experiment, it was found that significant level of change took place in all ages.

TABLE 4

Mean HR (beats/min)

| Age | Gender | Before use | After use (20 minutes) | Rate of change (%) |
|---|---|---|---|---|
| Twenties | Male (n = 5) | 71.33 | 66.16 | −7.25% |
| | Female (n = 5) | 73.17 | 67.30 | −8.02% |
| Thirties | Male (n = 7) | 72.76 | 67.08 | −7.81% |
| | Female (n = 3) | 75.21 | 68.85 | −8.46% |
| Forties | Male (n = 4) | 73.11 | 67.22 | −8.06% |
| | Female (n = 3) | 74.94 | 68.26 | −8.91% |
| Fifties | Male (n = 8) | 72.55 | 67.24 | −7.32% |
| | Female (n = 5) | 74.81 | 68.05 | −9.04% |
| Sixties | Male (n = 4) | 70.34 | 63.81 | −9.28% |
| | Female (n = 4) | 73.25 | 65.70 | −10.31% |

In the meantime, Table 5 shows the mean value (mean RR(ms)) of the time value between heat beats before and after using the apparatus 100 for stimulating the vagus nerve of the present invention. The QRS wave, which is the waveform of the electrocardiogram, indicates depolarization of the ventricle, namely, contraction of the ventricle. The change in R-R interval is used to check the activation condition of the sympathetic and parasympathetic nerve systems. For a healthy person, the value of RR interval increases, which means that the heart rate is decreased and simultaneously, the parasympathetic nerve system is activated.

TABLE 5

Mean RR (ms)

| Age | Gender | Before use | After use (20 minutes) | Rate of change (%) |
|---|---|---|---|---|
| Twenties | Male (n = 5) | 731 | 787 | 7.66% |
| | Female (n = 5) | 704 | 770 | 9.38% |
| Thirties | Male (n = 7) | 720 | 781 | 8.47% |
| | Female (n = 3) | 689 | 764 | 10.89 % |
| Forties | Male (n = 4) | 717 | 791 | 10.32% |
| | Female (n = 3) | 677 | 759 | 12.11% |
| Fifties | Male (n = 8) | 701 | 783 | 11.70% |
| | Female (n = 5) | 663 | 736 | 11.01% |
| Sixties | Male (n = 4) | 704 | 780 | 10.80% |
| | Female (n = 4) | 670 | 748 | 11.64% |

That is, according to the embodiment of the present invention, the nervous tissue within the human body is stimulated in the con-contact form which is more advanced than the non-invasive method of the conventional magnetic field therapy device. The object is stimulated using a fine magnetic field of a size in which the size of the magnetic field reaching a specific part (heart and/or vagus nerve) is able to be synchronized with the biomagnetic signal, such that the parasympathetic nerve is activated harmlessly to the human body. This method is completely different from that the conventional magnetic field therapy device treats diseases with strong stimulation. The method has the effect of eliminating the possibility of occurrence of various side effects that may be caused by the magnetic field. Particularly, the vagus nerve is stimulated by simply wearing the apparatus 100 around the neck, such that the parasympathetic nerve is activated within a short time, which provides high utility and usability.

Some embodiments omitted in this specification are equally applicable when their implementation subjects are the same. Also, various substitutions, modifications, and changes from the spirit of the present invention defined in the following claims by those skilled in the art are also included in the scope of the present invention, so that the present invention described above is not limited to the embodiments and the accompanying drawings.

The invention claimed is:

1. An apparatus for stimulating a vagus nerve, the apparatus comprising:
   a magnetic field generation unit generating a magnetic field in a form of a pulse wave, which is configured to stimulate a preset area including the vagus nerve of a user by an electric current applied to a coil;
   a power supply unit applying the electric current to the coil; and
   a control unit controlling an intensity of the electric current applied to the coil, and a pulse width and a peak interval of the magnetic field,
   wherein the magnetic field has a peak intensity that is set using a biomagnetic signal of the user,
   wherein the peak interval of the magnetic field between a falling edge and a subsequent rising edge is 20 to 400 milliseconds,
   wherein the pulse width of the magnetic field is 10 to 200 microseconds,
   wherein the peak intensity is 0.01 to 100 microteslas, and wherein the magnetic field generation unit further includes a silicon steel plate around which the coil is wound, the silicon steel plate having a length from 10 to 60 mm, a width from 10 to 60 mm, and a thickness from 0.1 to 5 mm, the coil having a diameter from 0.1 to 0.8 mm and being wound around the silicon steel plate 100 to 600 times.

2. The apparatus of claim 1, wherein the peak intensity is set using a distance between the magnetic field generation unit and the vagus nerve of the user and an intensity corresponding to a magnetic signal of the vagus nerve, and is set in such a manner that an intensity of the magnetic field which reaches the vagus nerve corresponds to an intensity of a magnetic field which is generated in the vagus nerve.

3. The apparatus of claim 1, wherein the peak intensity is set using a distance between the magnetic field generation unit and a heart of the user and an intensity corresponding to a magnetic signal of the heart, and is set in such a manner that an intensity of the magnetic field which reaches the heart corresponds to an intensity of a magnetic field which is generated in the heart.

4. The apparatus of claim 1, further comprising:
a housing containing the magnetic field generation unit, the power supply unit, and the control unit; and
a string member connected to the housing in such a manner as to be configured to hang the housing on a neck of the user, the string member adjusting a length in such a manner that the magnetic field generation unit is positioned within a preset distance from the vagus nerve of the user.

5. The apparatus of claim 1, wherein the magnetic field is repeated with a frequency of 1 to 8 Hz.

6. The apparatus of claim 1, wherein the apparatus is implemented in the form of a necklace, and the power supply unit is embedded within the apparatus in the form of a rechargeable battery, the apparatus further comprising:
a housing containing the magnetic field generation unit, the power supply unit, and the control unit; and
a string member connected to the housing in such a manner as to be configured to hang the housing on a neck of the user, the string member having an adjustable length to position the magnetic field generation unit in the housing within a preset distance from the heart of the user.

7. The apparatus of claim 1, wherein the diameter of the coil is from 0.2 to 0.4 mm.

8. The apparatus of claim 7, wherein a magnetic field effective radius of the magnetic field generation unit is about 30 cm.

9. The apparatus of claim 1, wherein the apparatus is implemented in the form of a blanket or a pillow, and the magnetic field generation unit is a first magnetic field generation unit, the apparatus further comprising:
a housing containing the control unit and the power supply unit; and
a second magnetic field generation unit, the first and second magnetic field generation units being arranged at a preset interval in the blanket or the pillow.

10. The apparatus of claim 1, wherein a magnetic field effective radius of the magnetic field generation unit is about 30 cm.

11. A method of stimulating a vagus nerve, the method comprising:
generating, by a magnetic field generation unit, a magnetic field in a form of a pulse wave, which stimulates an area including the vagus nerve of a user by applying an electric current to a coil; and
controlling an intensity of the electric current applied to the coil, and a pulse width and a peak interval of the magnetic field,
wherein the magnetic field has a peak intensity that is set using a biomagnetic signal of the user,
wherein the peak interval of the magnetic field between a falling edge and a subsequent rising edge is 20 to 400 milliseconds,
wherein the pulse width of the magnetic field is 10 to 200 microseconds,
wherein the peak intensity is 0.01 to 100 microteslas, and
wherein the magnetic field generation unit further includes a silicon steel plate around which the coil is wound, the silicon steel plate having a length from 10 to 60 mm, a width from 10 to 60 mm, and a thickness from 0.1 to 5 mm, the coil having a diameter from 0.1 to 0.8 mm and being wound around the silicon steel plate 100 to 600 times.

* * * * *